United States Patent
Bornack

(10) Patent No.: US 11,857,815 B2
(45) Date of Patent: Jan. 2, 2024

(54) PROTECTIVE EQUIPMENT COMPRISING A SENSOR DEVICE

(71) Applicant: Bornack GmbH & Co. KG, Ilsfeld (DE)

(72) Inventor: Klaus Bornack, Mundelsheim (DE)

(73) Assignee: Bornack GmbH & Co. KG, Ilsfeld (DE)

( * ) Notice: Subject to any disclaimer, the term of this patent is extended or adjusted under 35 U.S.C. 154(b) by 442 days.

(21) Appl. No.: 16/645,822

(22) PCT Filed: Sep. 11, 2018

(86) PCT No.: PCT/EP2018/074400
§ 371 (c)(1),
(2) Date: Mar. 10, 2020

(87) PCT Pub. No.: WO2019/048692
PCT Pub. Date: Mar. 14, 2019

(65) Prior Publication Data
US 2020/0276462 A1    Sep. 3, 2020

(30) Foreign Application Priority Data
Sep. 11, 2017 (DE) .................... 10 2017 120 925.5

(51) Int. Cl.
  *A62B 35/00*  (2006.01)
  *A41D 1/00*  (2018.01)
  (Continued)

(52) U.S. Cl.
  CPC .......... *A62B 35/0025* (2013.01); *A41D 1/002* (2013.01); *A41D 13/018* (2013.01);
  (Continued)

(58) Field of Classification Search
  None
  See application file for complete search history.

(56) References Cited

U.S. PATENT DOCUMENTS 3,123,831 A      3/1964 Wells et al.
2002/0156509 A1*  10/2002 Cheung .................. A61F 7/007
                                                607/108

(Continued)

FOREIGN PATENT DOCUMENTS

| DE | 195 45 864 A1 | 6/1997 |
| DE | 10 2009 056 744 A1 | 6/2011 |
| EP | 1 171 204 B1 | 1/2002 |
| EP | 3525891 A1 | 8/2019 |
| WO | 2012/158554 A2 | 11/2012 |

OTHER PUBLICATIONS

Summons to Oral Proceedings Under Rule 115(1) EPC; pp. 1-8; Feb. 21, 2022; European Patent Office; Postbus 5818; 2280 HV Rijswijk, The Netherlands.

*Primary Examiner* — Jay B Shah
(74) *Attorney, Agent, or Firm* — Robert A. Blaha; Smith Tempel Blaha LLC

(57) ABSTRACT

Protective equipment for protecting a person from an emergency situation is disclosed. The protective equipment has a securing device, which is portable by the person, having a securing system for protecting the person from an emergency situation. Furthermore, the protective equipment has a sensor device for detecting a dangerous situation prior to the emergency situation of the person, when the sensor device is coupled with the securing system in such a way that upon detection of the dangerous situation of the person, the sensor device automatically sets the securing system in a securing state for protecting the person.

10 Claims, 2 Drawing Sheets

(51) Int. Cl.
*A41D 13/018* (2006.01)
*A61B 5/0205* (2006.01)
*A61B 5/00* (2006.01)
*B63C 9/125* (2006.01)
*G08B 21/04* (2006.01)
*A61B 5/024* (2006.01)
*A61B 5/08* (2006.01)

(52) U.S. Cl.
CPC ........ *A61B 5/02055* (2013.01); *A61B 5/6804* (2013.01); *A62B 35/0075* (2013.01); *A62B 35/0093* (2013.01); *B63C 9/1255* (2013.01); *G08B 21/0446* (2013.01); *A61B 5/02438* (2013.01); *A61B 5/0816* (2013.01); *A61B 2560/0252* (2013.01); *A61B 2560/0257* (2013.01); *A61B 2562/029* (2013.01)

(56) References Cited

U.S. PATENT DOCUMENTS

| | | | |
|---|---|---|---|
| 2004/0003455 A1* | 1/2004 | Davidson | A41D 13/018 2/455 |
| 2006/0288464 A1* | 12/2006 | Warden | A41D 13/018 2/69 |
| 2008/0072942 A1 | 3/2008 | Warren | |
| 2009/0280705 A1* | 11/2009 | Puls | B63C 9/0005 340/573.6 |
| 2011/0103558 A1 | 5/2011 | Hooten | |
| 2014/0118498 A1 | 5/2014 | Lee et al. | |
| 2015/0027808 A1 | 1/2015 | Baillargeon et al. | |
| 2015/0375021 A1 | 12/2015 | Kozuki | |
| 2016/0183607 A1 | 6/2016 | Lopez Yunez et al. | |
| 2016/0220153 A1* | 8/2016 | Annegarn | A61B 5/7275 |
| 2017/0164675 A1* | 6/2017 | Buchert | A42B 1/008 |
| 2017/0202279 A1* | 7/2017 | Mazzarolo | G05B 15/02 |
| 2017/0243457 A1 | 8/2017 | Milbrand | |

\* cited by examiner

PROTECTIVE EQUIPMENT COMPRISING A SENSOR DEVICE

CROSS-REFERENCE TO RELATED APPLICATION

The present application is a U.S. national phase application that emerged from the International Application No. PCT/EP2018/074400 filed Sep. 11, 2018, which designated the U.S. and claims priority to German Patent Application No. 10 2017 120 925.5 filed Sep. 11, 2017, the entire contents of both of which are hereby incorporated herein by reference in their entirety.

TECHNICAL FIELD

Embodiments of the invention relate to protective equipment for protecting a person from an emergency situation. Furthermore, embodiments of the present invention relate to a method for protecting a person from an emergency.

TECHNOLOGICAL BACKGROUND

When working in dangerous working environments, such as for example at great heights or in critical environmental conditions, there is a permanent risk that the worker will find himself in emergency situations, which risk the life of the worker.

For example, when working under low ambient temperatures, the worker may quickly attain a hypothermia and requires a rescue from an according emergency situation. Furthermore, when working at great heights, there is a permanent risk of a fall from heights (or a crash). In order to secure people in this respect, for example, various types of fall protection devices are available. For example, various rope securing systems are being used, which are to mechanically absorb (or catch, or cushion) a fall (or crash) of the person in an emergency situation. This may lead to injuries, such as for example crushing injuries or whiplash injuries.

Airbags in motorcycle protective clothing, for example, as protective cushioning against a collision on the road are known for damping the shock of collision on the road. Furthermore, airbags in cars are known in this respect as protective cushioning for damping a collision.

SUMMARY

There may a need to protect a person even before the occurrence of an emergency situation and/or to avoid an emergency situation.

This need is satisfied by a protective equipment for protecting a person in an emergency situation and a method for protecting a person in an emergency situation according to the independent claims.

According to a first aspect of the present invention, there is described a protective equipment for protecting a person from an emergency situation. The protective equipment has a securing device, which is portable (or wearable) by the person, having a securing system for protecting the person from an emergency situation. Furthermore, the protective equipment has a sensor device for detecting a dangerous situation prior to (or before) the emergency situation of the person, wherein the sensor device is coupled (directly or via a control unit) with the securing system in such a way that upon detecting the dangerous situation of the person, the sensor device automatically (or self-actingly) sets (or adjusts) the securing system in a securing state (or protection condition) for protecting the person.

According to a further aspect of the present invention, there is described a method for protecting a person from an emergency situation. The method has protecting a person by a securing system of a securing device, which is portable (or wearable) by the person. Furthermore, a dangerous situation prior to (or before) the emergency situation of the person is detected by a sensor device which is coupled with the securing system. The sensor device is coupled with the securing system in such a way that upon detecting the dangerous situation of the person, the sensor device automatically (or self-actingly) sets (or adjusts) the securing system in a securing state (or protection condition) for the protection of the person.

Overview of Embodiments

An emergency situation may define a situation of the person, in which the latter may have already had an accident, for example. Such an emergency situation may, for example, represent a fall from heights (or a crash) of a person or a hypothermia of a person. The dangerous situation may refer to a situation in particular prior to (or before) the emergency situation. In other words, the dangerous situation may be detected by the sensor device already before the occurrence of an emergency situation may occur, and the securing state may be set. The dangerous situation may occur, for example, if the distance of the person from a fall edge or the body temperature of the person are below a threshold value.

The securing state may refer to the state, in which the user may be protected so that no emergency situation of the user may occur. In the above-mentioned examples, for example, a safety rope of the securing system may be tensioned so that a fall may be prevented, or, as described below, a temperature-control device may warm the person in order to prevent a hypothermia (i.e., the emergency situation).

With the present invention, in particular, the sensor device may, after the detection of the dangerous situation, automatically, i.e. without manual intervention of the person or another person, activate the securing system and set it in a securing state. For this purpose, the sensor device may be coupled directly with the securing system or indirectly via a control unit. The sensor device itself or the control unit may act as a command generator for the securing system in order to set it in the securing state. The sensor device may send in particular electrical, optical or electromagnetic control signals to the securing system. The sensor device may be in particular an electronic sensor device.

Examples of the sensor device, the securing device and the securing system are given in the following.

According to an exemplary embodiment, the sensor device may have at least a position sensor, an acceleration sensor and/or a motion sensor.

The position sensor may be, for example, a GPS sensor which may determine GPS data in order to determine an exact geographical and/or spatial position of the person. If the person is, for example, in a dangerous situation, for example in a predetermined area in front of a fall edge, the securing state of the securing system may be set from this (or on this basis).

By the acceleration sensor, for example, a position and/or acceleration of the person may be measured. With the motion sensor a speed of the person may be measured. If the person exceeds, for example, a particular speed, as for example in the case of a fall, the defined dangerous situation (fast fall) may occur, so that the securing system assumes the securing state in order to prevent a further fall and thus an impact (corresponds to the emergency situation) of the person on the ground.

By the position sensor and/or the acceleration sensor, furthermore, the position (horizontal and/or vertical) of the person may be determined. If, for example, the person is lying in a horizontal position, a dangerous state of the person may be assumed, so that the securing system may be activated on this basis.

Furthermore, for example, a change in the path (horizontal or vertical) of a moving person may be measured, e.g. by the position sensor and/or by the acceleration sensor. In the event of a deviation from a permissible path or in the event of a leaving of a movement field of the person, the sensor device may thus activate the securing system.

Furthermore, the protective equipment according to the invention and/or the sensor device thereof may be used as a secondary securing system. Thus, for example, in the event of a failure of a primary securing system, the protective equipment according to the invention may act as an emergency stop. If, for example, a fall protection system fails as a primary securing system, such as for example a roping device having a fall stop function, which may fix the rope length of a safety rope at a defined fall speed, the secondary securing equipment according to the present invention may be activated. The same may apply, for example, to a rope-down device as a securing system. If the limited rope-down speed (which is measured by the sensor device) of the rope-down device is exceeded, an emergency stop/an additional brake may come into action. In this respect, the sensor device may, for example, detect a distance to the ground and activate the securing system upon falling below a minimum distance. The securing system may, for example, be the above-described fall protection device of the primary securing device, so that the sensor device may then fix the rope length or pulls in and may tighten a loose safety rope.

According to a further exemplary embodiment, the sensor device may have a distance sensor. The distance sensor may be configured to measure a distance to a predeterminable reference point and/or a danger point. The reference point (or reference location) may define, for example, a position in space, which may have a particular distance to a danger point, such as for example an obstacle or a fall edge. As soon as the distance between the person and the reference point falls below a predetermined target value, the securing system may be, for example, automatically set in the securing state.

The sensor device may have, for example, an optical sensor, an ultrasonic sensor and/or an infrared sensor, e.g. to measure a distance to a predeterminable reference point and/or a danger point and/or also to function as a position sensor.

Furthermore, the sensor device may have a height sensor in order to measure a height above a defined plane or reference surface (e.g. above the ground and/or above sea level). The critical height may, for example, be adjustable so that, upon falling below the critical height, the securing system may be, for example, automatically set in the securing state.

According to a further exemplary embodiment, the sensor device may have a medical sensor. The medical sensor may be configured to measure a medical condition (or medical state), in particular the body temperature, the respiratory frequency (or breathing rate) of the person and/or the heart rate. The medical sensor may accordingly have for example a body thermometer, a respiratory measuring device, a pulse measuring device and/or a blood measuring device for measuring blood. For example, if the person works in a cool working environment, there may be the risk of a hypothermia (corresponds to the emergency situation). If the body temperature of the person falls below a particular body temperature, the dangerous situation may occur. The sensor device accordingly may send control commands to the securing system in order to set a securing state. The securing state may be set, for example, by activating a body heater as a securing system or by sending an alarm in order to get the person out of the dangerous situation and/or out of the cold working environment in order to warm up the person.

In this way, an overexertion and/or a collapse of the person may be detected, and a securing state may be called up.

The medical condition may be transmitted to a supervisor and/or based on the medical condition the securing system may be automatically set in the securing state.

According to a further exemplary embodiment, the sensor device may have an environmental sensor for measuring environmental parameters, in particular the ambient temperature, the ambient wind, the ambient air pressure and/or the ambient humidity. Accordingly, the sensor device may represent a thermometer, an anemometer, a barometer or a hygrometer.

If the person is, for example, working on an offshore platform or a wind turbine installation, the person may be exposed to high wind speeds and storms. If, for example, a predefined threshold wind speed is measured by the sensor device, a safety rope as a securing system, for example, may be automatically tightened in order to ensure the safety of the person.

By the measurement of the air pressure, for example, a change in height (fall height) may be detected and a securing state may be set (or adjusted), for example by tightening a safety rope.

According to a further exemplary embodiment, the portable securing device has a rope-up protection, in particular a safety belt, a protective clothing, in particular a protective jacket or a protective overall, a protective shoe and/or a respiratory protection.

The securing system and/or the sensor device may be, for example, integrated and fixed in the securing device so that the person may permanently carry the securing system and the sensor device with the securing device. For example, the protection system and the sensor device may be arranged at a safety belt as a securing device. Thereby, the person may not be restricted in his or her freedom of movement.

According to a further exemplary embodiment, the securing system may have a fall protection device (or fall arrester). The fall protection device may be equipped with a safety rope and may be configured to control the length of a rope length of the safety rope between the portable securing device and a securing point for fixing the safety rope. The fall protection device may be coupled with the sensor device in such a way that the rope length may be controllable in dependency of the detection of the dangerous situation.

In this case, the fall protection device may have, for example, a rope winch, which may for example be operated electrically. The safety rope may be wound onto the rope winch. If the sensor device detects a dangerous situation, for example if a distance to a fall site (or crash site) is undershot or a fall speed is detected, the sensor device may control the rope winch in the securing state. Herein, the rope winch may, for example, abruptly fix the length of the safety rope by fixing the rope winch.

In addition, the fall protection device may have a rope brake, which may reduce an unwinding speed of the safety rope from the rope winch.

According to a further exemplary embodiment, the securing system may have an airbag device. The airbag device may be configured to be inflatable in order to form a damping body in the inflated state, i.e. in the securing state. The airbag device may be coupled with the sensor device in such a way that the airbag device may be inflatable in dependency of the detection of the dangerous situation. If, for example, a distance to an obstacle and/or a danger point is reduced or a fall speed is detected, the sensor device may activate the airbag device. Since the sensor device already may detect a dangerous situation, which may be defined in terms of time or space before the emergency situation occurs, more time may thus be enabled (or allowed) to activate the airbag system, so that a better protection may be achieved as compared to a pure impact detection, in which the emergency situation may have already occurred when the airbag is activated.

According to a further exemplary embodiment, the airbag device may be configured as an inflatable life jacket. For example, the sensor device may have a moisture meter which measures the ambient moisture in the person's surroundings. If the sensor device detects, for example, that the person is in a liquid medium, such as for example water, the airbag device may be activated as a life jacket.

According to a further exemplary embodiment, the securing system may have a temperature-control device, wherein the temperature-control device may be configured to temperature-control (or temper) the portable securing device. The temperature-control device may be coupled with the sensor device in such a way that the temperature-control device may be controlled in dependency of the detection of the emergency situation in order to achieve the securing state. The temperature-control device may be integrated in the securing device, for example in the safety jacket or a safety belt, in such a way that the temperature-control device may be present between the person and the securing device in order to achieve a good heating effect. The temperature-control device may, for example, have a resistance heater.

Furthermore, the temperature-control device may have a temperature-control medium, which may flow through corresponding temperature-control channels in order to achieve a temperature-control effect. The temperature-control medium may be used as a heating medium or a cooling medium. If, for example, a particular degree of hypothermia of the person is detected, the temperature-control unit may be configured to heat the person. If the person is working in a hot environment, the temperature-control device may be configured as a cooling device and accordingly may generate a cooling effect, for example when measuring an increased body temperature. The temperature-control device as a cooling device may operate, for example, according to the principle of evaporative cooling and may, for example, have a compressor for compressing the cooling medium.

According to a further exemplary embodiment, the securing system may have an alarm device. The alarm device may be configured to send an alarm signal that may be indicative of the dangerous situation to a monitoring station. The alarm device may be coupled with the sensor device in such a way that in dependency of the detection of the emergency situation, the alarm device may send the alarm signal indicative of the dangerous situation and the securing state may be settable (or adjustable) to protect the person. The alarm device may generate, for example, an optical, acoustic or electrical warning signal. The monitoring station may be located spatially at a distance from the securing system. The alarm signal may be sent, for example, wirelessly to the monitoring station.

In particular, the sensor device may send the sensor data to the monitoring station. Herein, for example, a dangerous situation and/or an emergency situation may be detected by a supervising person, even if the supervising person is not on site with the person. In other words, a remote diagnosis may become possible.

According to a further exemplary embodiment, the sensor device may be coupled with the securing system in such a way that sensor data of the sensor device may be transmittable by wire or wireless. As a wireless transmission technique, for example, an NFC (Near Field Communication) connection, a radio connection using electromagnetic waves (radio waves), or a transponder connection may be usable. Furthermore, signals may be transmitted, for example, via optical waveguides, which may couple the sensor device with the securing system.

It is pointed out that the embodiments described herein represent only a limited selection of possible embodiment variants of the invention. Thus, it is possible to combine the features of individual embodiments in a suitable manner, so that for the skilled person with the here explicit embodiments a plurality of different embodiments are to be considered as obviously disclosed. In particular, some embodiments of the invention are described by device claims and other embodiments of the invention by process claims. However, it will immediately become clear to the person skilled in the art upon reading this application that, unless explicitly stated otherwise, in addition to a combination of features that belong to one type of subject matter of the invention, also an arbitrary combination of features that belong to different types of subject matter of the invention is also possible.

BRIEF DESCRIPTION OF THE DRAWINGS

For further explanation and better understanding of the present invention, embodiment examples are described in the following with reference to the appended drawings. In the drawings.

DETAILED DESCRIPTION OF EXEMPLARY EMBODIMENTS

Figure 1:
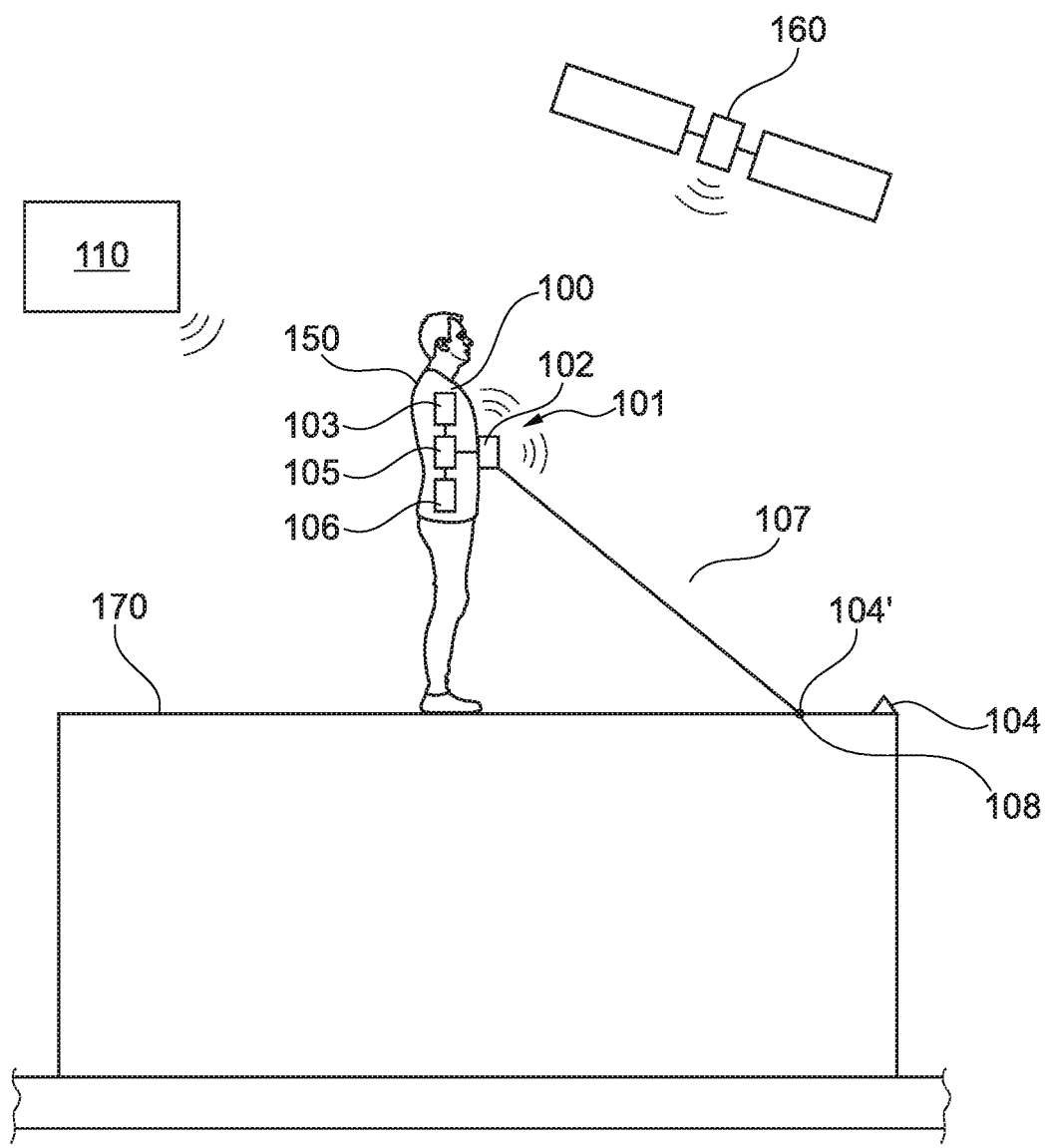
FIG. 1 is a schematic illustration of a person with a protective equipment according to an exemplary embodiment of the present invention.

Same or similar components in different figures are provided with the same reference numerals. The representations in the figures are schematically presented.

FIG. 1 shows a protective equipment 100 for protecting a person 150 from an emergency situation. The protective equipment 100 may have a securing device 101, which may be portable (or wearable) by the person 150, having a securing system 102 for protecting the person 150 from an emergency situation. Furthermore, the protective equipment 100 may have a sensor device 103 for detecting a dangerous situation prior to (or before) the emergency situation of the person 150, wherein the sensor device 103 may be coupled with the securing system 102 directly or indirectly via a control unit 105 in such a way that upon detection of the dangerous situation of the person 150, the sensor device 103 may automatically set the securing system 102 in a securing state for protecting the person 150.

In the exemplary embodiment in FIG. 1, the person 150 may be located on a working area 170. The working area 170 may represent, for example, an elevated platform, such as a container. A danger point 104 may be defined on the edges and/or borders of the work area 170, since the person 150 may fall (or crash) over the edge upon passing over the danger point 104. In this respect, a danger point 104 may be defined at a distance from the edge. In this way, it may be defined already before the fall of the person 150 that a dangerous situation may exist and the securing system may have to be activated.

The person 150 in FIG. 1 may wear, for example, a rope-up protection, in particular a safety belt, as a securing device 101.

The securing system 102 may have a fall protection device (or fall arrester). The fall protection device may be equipped with a safety rope 107, and may be configured to control the length of a rope length of the safety rope 107 between the portable securing device 101 and a securing point 108 for fixing the safety rope 107. The fall protection device may be coupled with the sensor device 103 in such a way that the rope length may be controllable in dependency of the detection of the dangerous situation.

In this case, the fall protection device may have, for example, a rope winch which may, for example, be operated electrically. The safety rope 107 may be wound onto the rope winch. If the sensor device 103 detects a dangerous situation, for example if a distance to a fall point (e.g. distance between reference point 104' and danger point 104) is undershot or a fall speed is detected, the sensor device 103 may control the rope winch in the securing state. In doing so, the rope winch may, for example, abruptly fix the length of the safety rope 107 by fixing the rope winch. In addition, the fall protection device may have a rope brake, which may reduce an unwinding speed of the safety rope 107 from the rope winch.

The sensor device 103 may have at least a position sensor, an acceleration sensor and/or a motion sensor. The position sensor may be, for example, a GPS sensor which may determine GPS data from a satellite 160 in order to determine an exact geographical and/or spatial position of the person 150. If the person 150 is, for example, in a dangerous situation, for example at a predetermined reference point 104' in front of a fall edge 104, the securing state of the securing system may be set from this (or on this basis).

Sensor device 103 may also include a distance sensor. The distance sensor is configured to measure a distance to the predeterminable reference point 104' and/or the danger point 104. The reference point 104' may define, for example, a position in space which may have a particular distance to a danger point 104, such as for example the fall edge. As soon as the distance between the person 150 and the reference point falls below a predetermined target value (or setpoint), the securing system 102, i.e. the fall protection device, may be, for example, automatically set in the securing state.

The securing system 102 and/or the sensor device 103 may be integrated and fixed in the securing device 101, so that the person 150 may be permanently carrying, with the securing device 101, the securing system 102 and the sensor device 103.

In particular, the sensor device 103 may send the sensor data to the monitoring station 110, for example by means of a transmission unit 106. Herein, for example, a dangerous situation or an emergency situation may be detected by a supervising person, even if this person may not be on site with the person 150. Thus, in other words, a remote diagnosis may become possible.

Figure 2:
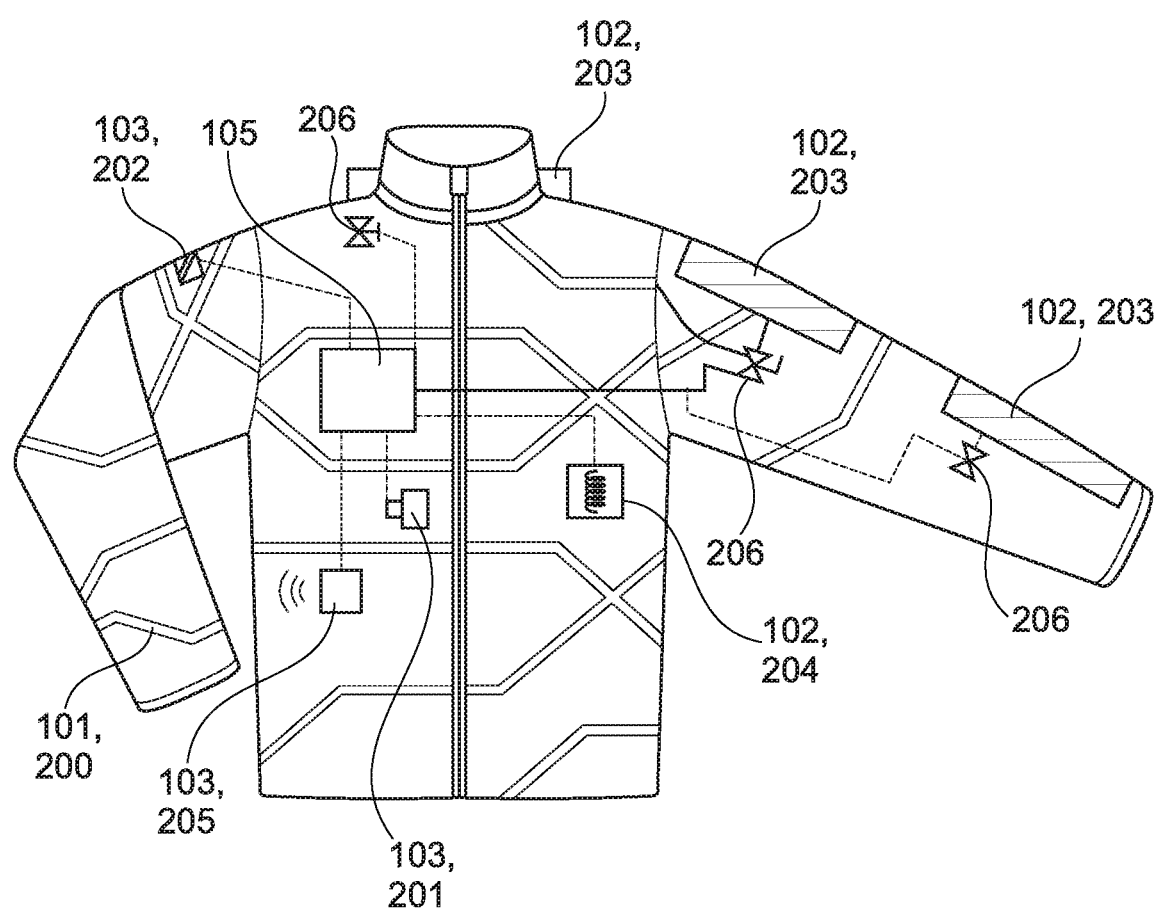
FIG. 2 is a schematic illustration of a protective equipment with a protective jacket as a securing device according to an exemplary embodiment of the present invention.

FIG. 2 shows a protective jacket 200 as a securing device 101. The securing system 102 and the sensor device 103 may be integrated in the protective jacket 200.

The securing system 102 may have, for example, an airbag device 203. The airbag device 203 may be embodied to be inflatable in order to form a damping body in the inflated state, i.e. in the securing state. The airbag device 203 may be coupled with the sensor device 103 in such a way that the airbag device 203 may be inflatable in dependency of the detection of the dangerous situation. If, for example, a distance to an obstacle or a dangerous point is reduced or a fall speed is detected, the sensor device 103 may activate the airbag device 203. Since the sensor device 103 may detect already a dangerous situation, which may be defined in terms of time or space before the emergency situation occurs, more time may thus be enabled for activating the airbag device 203, so that better protection may be achieved with respect to a pure impact detection, in which the emergency situation may have already occurred when the airbag may be activated. The airbag device 203 may, for example, be controlled by controlling control elements and/or valves 206.

The protective jacket 200 may have, for example, a medical sensor 201 as a sensor device 103. The medical sensor 201 may be configured to measure a medical condition, in particular the body temperature, the respiratory frequency of the person 150 and/or the heart rate. The medical sensor 201 may accordingly have, for example, a body thermometer, a respiratory measuring device, a pulse measuring device and/or a blood measuring device for measuring blood. For example, if the person 150 works in a cool working environment, there may be a risk of hypothermia (corresponds to the emergency situation). If the body temperature of the person 150 falls below a particular body temperature, the dangerous situation may occur. The medical sensor 201 accordingly sends control commands to the securing system 102 in order to set the securing state.

In this respect, the securing system 102 may have, for example, a temperature-control unit 204. The securing state may be set, for example, by configuring the temperature-control unit 204 as a body heater to increase the body heat of the person 150.

The sensor device 103 may also have an environmental sensor 202 that may be integrated in the protective jacket 200 for measuring environmental parameters, in particular the ambient temperature, the ambient wind, the ambient air pressure and/or the ambient humidity. By the measurement of the air pressure, for example, a change in height (fall height) may be determined and a securing state may be set, for example by tightening a safety rope 107 (see FIG. 1).

Furthermore, an alarm device 205 may be arranged in the protective jacket 200 as a securing system 102. The alarm device 205 may be configured to send an alarm signal that may be indicative of the dangerous situation to a monitoring station 110 (see FIG. 1). The alarm device 205 may be coupled with the sensor device 103 in such a way that the alarm device 205 may generate the alarm signal in dependency of the detection of the dangerous situation and, for example, the safety condition for protecting the person 150 may be settable. The alarm device 205 may generate, for example, an optical, acoustic or electrical warning signal. The monitoring station 110 may be located at a distance from the securing system 102. The alarm signal may be sent, for example, wirelessly to monitoring station 110.

Supplementarily, it should be noted that "comprising" does not exclude other elements or steps and that the article "a" or "an" does not exclude a plurality. Furthermore, it is noted that features or steps, which are described with reference to one of the above embodiments, can also be used in combination with other features or steps of other examples described above.

LIST OF REFERENCE NUMERALS 100 protective equipment
101 securing device
102 securing system
103 sensor device
104 reference point/danger point
105 control unit
106 transmission unit
107 safety rope
108 securing point
110 monitoring station
150 person
160 GPS satellite
170 working area
200 protective jacket
201 medical sensor
202 environmental sensor
203 airbag device
204 temperature-control unit
205 alarm device
206 control element/valve

The invention claimed is:

1. A protective equipment for protecting a person, the protective equipment comprising: a securing device, which is wearable by the person, having a securing system for protecting the person from a fall, a sensor device for detecting a distance between the person and a reference point, wherein the sensor device is coupled with the securing system in such a way that upon detecting when the distance between the person and the reference point is below a threshold value, the sensor device automatically sets the securing system in a securing state for protecting the person from the fall; wherein the sensor device has a distance sensor, wherein the distance sensor is arranged to measure a distance to at least one of the reference point and a fall edge, wherein the wearable securing device is connected to a rope, wherein the securing system is configured to control a length of the rope between the wearable securing device and a securing point for fixing the rope, such that the distance between the person and the reference point is kept below the threshold value, wherein the securing device is coupled to the sensor device in such a way that the length of the rope is controllable by at least one of a rope brake of the securing device and a drivable rope winch of the securing device.

2. The protective equipment according to claim 1, wherein the sensor device has at least one of a position sensor, an acceleration sensor, and a motion sensor, in addition to the distance sensor.

3. The protective equipment according to claim 1, wherein said sensor device has a medical sensor arranged to measure a medical condition, wherein the medical sensor is in addition to the distance sensor.

4. The protective equipment according to claim 1, wherein the sensor device has an environmental sensor for measuring environmental parameters, wherein the environmental sensor is in addition to the distance sensor.

5. The protective equipment according to claim 1, wherein the securing system has an airbag device, wherein the airbag device is embodied inflatable to form a damping body in the inflated state,
wherein the airbag device is coupled to the sensor device in such a way that the airbag device is inflatable prior to the fall.

6. The protective equipment according to claim 5, wherein the airbag device is configured as an inflatable life jacket.

7. The protective equipment according to claim 1, wherein the securing system has a temperature-control device,
wherein the temperature-control device is configured to temperature-control the wearable securing device,
wherein the temperature-control device is coupled to the sensor device in such a way that the temperature-control device is controllable.

8. The protective equipment according to claim 1, wherein the securing system has an alarm device,
wherein the alarm device is configured to send an alarm signal indicative of when the distance between the person and the reference point is below the threshold value to a monitoring station,
wherein the alarm device is coupled to the securing device and a transmission unit in such a way that the alarm device sends the alarm signal and enables the securing state for protecting the person.

9. The protective equipment according to claim 1, wherein the sensor device is coupled with the securing system in such a way that sensor data of the sensor device are transmittable by wire or wirelessly.

10. A method for protecting a person from a fall, the method comprising:
providing a securing device wearable by the person, the securing device connected to a rope;
detecting a distance between the person and a reference point by a sensor device coupled with the securing device; and
controlling a length of the rope by at least one of a rope brake of the securing device and a drivable rope winch of the securing device,
wherein the sensor device is coupled with the securing device in such a way that when the distance between the person and the reference point is below a threshold value, the sensor device automatically sets the securing system in a securing state for protecting the person,
wherein the sensor device has a distance sensor,
wherein the distance sensor is arranged to measure a distance to at least one of the reference point and a fall edge.

* * * * *